US009858729B2

(12) United States Patent
Keller et al.

(10) Patent No.: US 9,858,729 B2
(45) Date of Patent: Jan. 2, 2018

(54) PIPETTE CHECK STATION

(71) Applicant: Mettler-Toledo Rainin, LLC, Oakland, CA (US)

(72) Inventors: Gerhard Keller, San Ramon, CA (US); Richard Hill, Berkeley, CA (US); Deryl Stanley, Livermore, CA (US); James Petrek, Danville, CA (US); Murray Anderson, San Ramon, CA (US)

(73) Assignee: Mettler-Toledo Rainin, LLC, Oakland, CA (US)

( * ) Notice: Subject to any disclaimer, the term of this patent is extended or adjusted under 35 U.S.C. 154(b) by 0 days.

(21) Appl. No.: 14/986,387

(22) Filed: Dec. 31, 2015

(65) Prior Publication Data
US 2017/0193712 A1 Jul. 6, 2017

(51) Int. Cl.
*G07C 1/08* (2006.01)
*B01L 9/00* (2006.01)
*G06K 7/10* (2006.01)
*G06F 17/30* (2006.01)
*G06F 19/00* (2011.01)

(52) U.S. Cl.
CPC ............... *G07C 1/08* (2013.01); *B01L 9/54* (2013.01); *G06F 17/30551* (2013.01); *G06F 17/30554* (2013.01); *G06F 19/3412* (2013.01); *G06K 7/10366* (2013.01); *B01L 2200/148* (2013.01); *B01L 2300/022* (2013.01); *B01L 2300/023* (2013.01); *B01L 2300/027* (2013.01)

(58) Field of Classification Search
CPC .... G07C 1/08; G07C 3/00; B01L 9/54; B01L 2300/027; B01L 2200/148; B01L 2300/022; B01L 2300/023; G06K 7/10366; G06F 17/30551; G06F 19/3412; G06F 17/30554; G06Q 10/0875
See application file for complete search history.

(56) References Cited

U.S. PATENT DOCUMENTS

| 6,845,279 | B1* | 1/2005 | Gilmore | G05B 19/406 340/426.1 |
|---|---|---|---|---|
| 8,368,518 | B1* | 2/2013 | Castrovinci | G06Q 10/0875 340/10.51 |
| 9,537,335 | B2* | 1/2017 | Furui | B25F 5/02 |
| 2008/0250797 | A1* | 10/2008 | Rozendaal | F25D 29/00 62/127 |
| 2011/0236981 | A1* | 9/2011 | Wakamiya | G01N 35/00663 436/52 |
| 2012/0095961 | A1* | 4/2012 | Meyer | G07C 3/00 707/634 |
| 2012/0143773 | A1* | 6/2012 | Clausen | G06Q 30/012 705/302 |
| 2012/0291567 | A1* | 11/2012 | Homberg | B01L 3/0237 73/864.13 |
| 2013/0266952 | A1* | 10/2013 | Goemann-Tho | B01L 3/021 435/6.12 |

(Continued)

Primary Examiner — Sonji Johnson
(74) Attorney, Agent, or Firm — Clarke A. Wixon

(57) ABSTRACT

A pipette check station for checking the calibration or service status of a pipette includes an RFID reader, a user interface with a display and buttons, and a digital interface to connect the check station to additional equipment; the check station optionally further includes provisions to hold pipettes for storage and to charge electronic pipettes held thereupon.

22 Claims, 13 Drawing Sheets

(56) References Cited

U.S. PATENT DOCUMENTS

2014/0257530 A1* 9/2014 Misoka ............... G05B 19/406
  700/79
2016/0048709 A1* 2/2016 Butler ................. H04L 67/1097
  340/10.51

* cited by examiner

PIPETTE CHECK STATION

FIELD OF THE INVENTION

The invention relates to air displacement pipetting reliability aids, and more particularly to an electronic station capable of automatically determining and displaying the calibration status of one or more pipettes.

BACKGROUND OF THE INVENTION

Handheld pipettes are commonly used to dispense or transfer small but accurately measured quantities of liquids.

Air displacement pipettes are the most common variety of handheld pipettes. In an air displacement pipette, a controllable piston is mounted for movement axially within a chamber in the pipette; the piston moves in response to either manual control (as described above) or motorized electronic control. Typically, the piston moves in a chamber in the liquid end, or shaft, of the pipette, to which disposable pipette tips may be mounted.

An air tight seal is formed between the piston and the shaft. With such a seal in place, axial movement of the piston will vary the size of the airspace within the shaft. Moving the piston downward, into the shaft, will reduce the airspace and force air out of the shaft through an open distal end. Moving the piston upward, out of the shaft, will increase the airspace and cause air to be drawn into the shaft through the open end.

A disposable pipette tip is then sealed to the open distal end of the shaft. Then, as the piston is moved within the shaft, air—or a measured quantity of liquid equal in volume to the displaced air—is drawn into or forced out of the tip. With both the piston and the tip sealed to the shaft, the only entry and exit path should be the distal open end of the disposable pipette tip. Because of the sealed system, air displacement pipette may be used to make accurate and precise measurements, and to move carefully calibrated quantities of liquids.

To function properly, then, not only do air displacement pipettes require a reliable seal between the tip and the shaft, but they also require a seal between the shaft and the piston. There are two seals, and two potential points of failure. The seal between the tip and the shaft is replaced every time a tip is discarded and replaced with a new one, but the seal in the pipette is serviced infrequently. This may lead to leaks and other failures, which in turn may lead to inaccuracy in liquid measurement or failure in pipetting operations.

In general, seal failure (such as wear, splitting, other damage, misalignment, dislodgment, corrosion, or contamination) is a common cause of pipetting failure. These failures can lead to failed outcomes, and may be difficult to identify in advance, or even as pipetting is ongoing. Wear and damage to the shaft in the tip mount region can also result in failures, and for this reason, plastic pipette shafts are also replaced from time to time.

These problems may be mitigated to some extent by performing frequent calibrations and having pipette serviced relatively often. Best practices in this regard frequently involve regular seal replacement, even if it does not appear necessary. However, because a damaged or leaking seal may not be visually evident, and slightly inaccurate pipetting results may be attributed to numerous other causes (user error, environmental conditions, etc.) or overlooked entirely, some users may tend to skip required or recommended pipette services—especially because such services may take a needed pipette out of use at an inconvenient time.

Many organizations track the calibration and service status of their pipettes by maintaining centralized records that correlate pipettes' serial numbers (or other individually trackable information, like asset tag numbers) to a listing of calibration or service dates. When a pipette comes up for a recommended service, an asset manager for the organization may then use these centralized records to identify where the pipette is kept, then either remove the pipette from the laboratory for service (if the pipette can be found) or alert a laboratory manager that service is required. If the pipette is out of place or unable to be located, or if the laboratory personnel are uncooperative, the service or calibration opportunity may be missed or significantly delayed, leading to potentially inaccurate results.

Some organizations also associate calibration and service requirements directly with each pipette, for example by affixing a small label to the pipette bearing recommended calibration or service dates. However, this is not an ideal solution, as such small labels may be easily overlooked, or the labels themselves may be dislodged or damaged through repeated handling, cleaning, or autoclaving. Adhesive labels may also be disfavored in some especially sensitive laboratory environments.

With either of these systems—centralized tracking and individual labeling—there is no integrated, centralized way to both manage and oversee pipette service and calibration while also tracking pipettes while they are in use.

Accordingly, there is a need for a simple, easy to operate system to manage and track pipette calibration and service status. Such a system would be ideally situated in a laboratory or other area where the pipetting is performed, and would provide information about the calibration and service status of pipettes in use within the laboratory with little or no manual intervention. A system for providing such information may take the form of a pipette check station, or even more advantageously a pipette storage stand or rack incorporating such pipette check functionality. Such a pipette check station may also facilitate periodic calibration spot-checks and provide a simple interface allowing a user to access additional pipetting-related products and services. A pipette check station may also provide information to a centralized asset tracking system, allowing an organization to maintain records of pipette use, calibration, and service events.

SUMMARY OF THE INVENTION

A pipette check station according to the invention addresses some long-felt needs relating to pipette calibration and service management in organizations where air displacement pipettes are used, as described above.

An embodiment of a system according to the invention comprises a pipette check station configured as a pipette stand with electronic pipette charging capability and further interactive capabilities. The stand includes one or more Radio Frequency Identification (RFID) reading coils or other antennas to read calibration or service data stored in a passive RFID transponder embedded in a pipette, and is programmed to read such data and present calibration and service information to a user whenever an RFID-enabled pipette is placed on the stand.

When a pipette with an embedded passive RFID transponder is serviced, a non-volatile memory chip is updated with information regarding the recommended next service date and next calibration date. Accordingly, when such a pipette is placed on a charge stand according to the invention, the stand can read the dates stored in the RFID transponder's memory, compare the stored dates to the current date, and determine whether the pipette is free to be used, due for calibration or service, or overdue for calibration or service. This information presented to the user in a friendly, understandable, graphic manner, and a data connection between the stand and other equipment can be used to update a remote user or a central database regarding pipette calibration and service status.

In an embodiment of the invention, the pipette check station comprises a four position pipette charge stand with a display screen, capable of holding both electronic and manual pipettes. The charge stand will charge up to four electronic pipettes at once, and will show the charge status for each pipette on the display screen while also showing the service and calibration status based upon information received from the RFID transponder. When a manual pipette is placed on the stand, only service and calibration status are displayed.

In an embodiment of the invention, some other data storage facility may be used in place of an RFID transponder—for example, a pipette or other item may be equipped with a bar code or other visual data, a Bluetooth or near-field communication (NFC) data source, an electrically coupled memory chip, or some other readable data source.

The pipette check station may also include one or more data communication interfaces, such as a USB or other serial interface (to exchange data with a connected computer workstation or to upgrade the firmware on the pipette check station), a wireless connection (such as Bluetooth or WiFi), or a wired network connection. One or more of these interfaces may also be configured to connect the pipette check station to an accessory. A pipette check station according to the invention may also be configured to use a remote display or user interface capabilities (such as a remote input device).

Preferably, the pipette check station may be physically configured in a number of advantageous arrangements, including but not limited to a benchtop pipette stand, or a pipette stand with a clamp, magnetic coupling, or other means of coupling to other laboratory surfaces.

The pipette check station may have some user controls, such as a set of navigation and selection buttons to facilitate configuration and interaction.

An embodiment of a pipette check station according to the invention may also include advanced e-commerce capabilities, such as the ability to request service or a consumable refill by interacting directly with the user controls and display screen on the check station.

Accordingly, a number of shortcomings of other known pipette calibration and service tracking and management schemes are addressed by using a system according to the invention. Pipettes are easily and simply identified and tracked, with calibration and service status readily visible to both users in the laboratory and managers elsewhere in the organization. This capability can lead to improved compliance with calibration and service standards, and reduced losses caused by inaccurate pipetting or equipment unexpectedly taken out of service.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
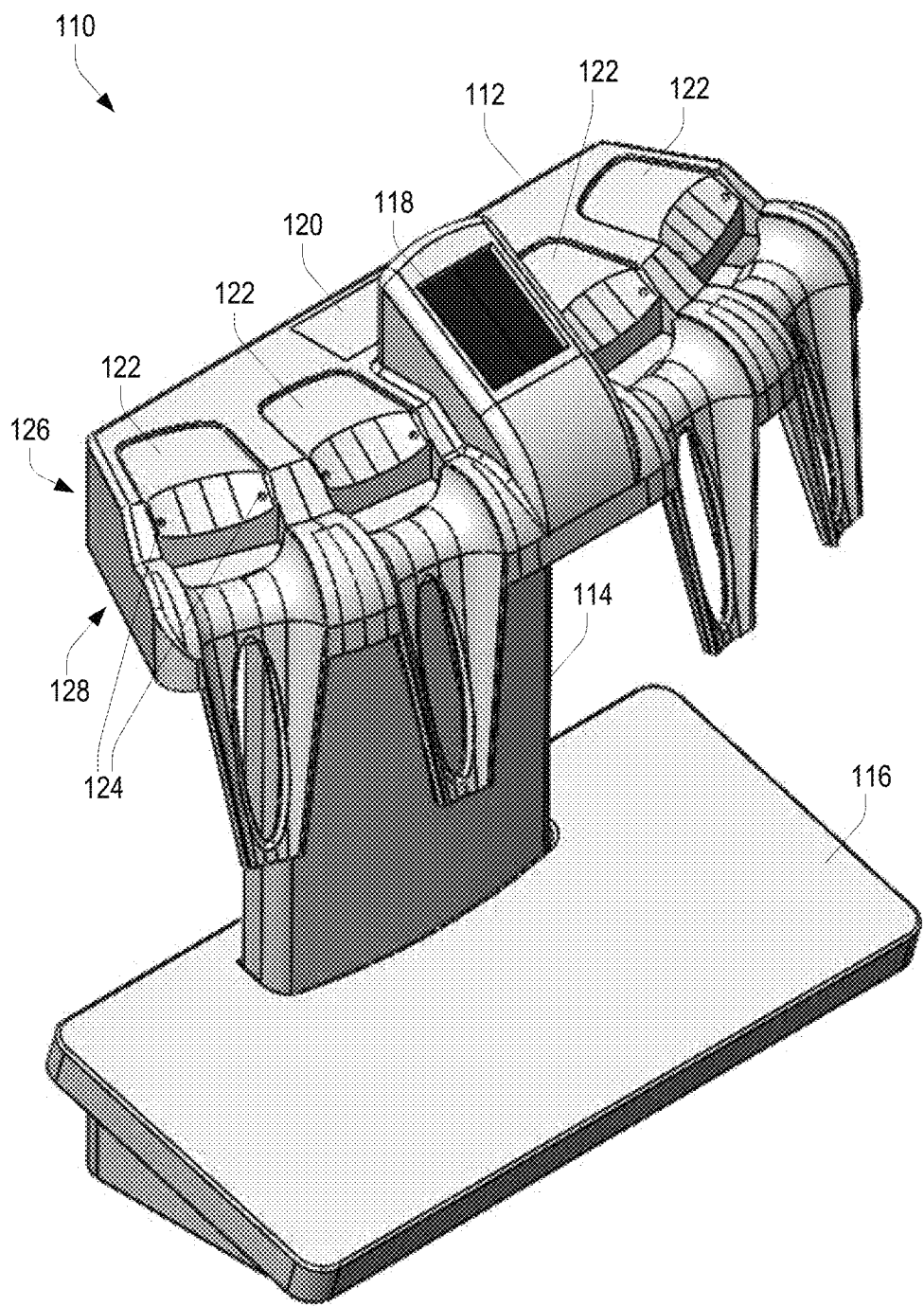
FIG. 1 illustrates a pipette check station according to the invention in the form of a four-position electronic pipette charge stand.

Referring initially to FIG. 1, a pipette check station 110 according to the invention is advantageously configured as a four-position electronic pipette charging stand. The check station 110 as illustrated includes three primary portions: a main body 112, a column 114, and a base 116. The base 116 provides a stable benchtop platform for the check station 110, while the column 114 ensures that the main body 112 holds pipettes an adequate and comfortable distance above the bench.

The body 112 includes a display screen 118, which in the disclosed embodiment is a dot matrix color LCD screen of the sort used on mobile telephones and other small devices. As will be discussed in further detail below, the display screen 118 presents a visual user interface for the pipette check station 110. Positioned to the rear of the display screen 118 is a control panel 120 with input buttons, illustrated in greater detail in FIG. 2 and described below. The body also includes four pipette stand positions 122, each with charging terminals 124. When one or more compatible electronic pipettes are placed in the pipette stand positions 122, the charging terminals 124 connect to coupling terminals on the electronic pipettes, completing circuits capable of replenishing rechargeable batteries in the pipettes. In a presently preferred embodiment of the invention the pipette check station 110 is capable of charging four electronic pipettes simultaneously, but it may also be configured to charge pipettes sequentially, or in an alternative embodiment may not be equipped with charging capabilities in some or all of the pipette stand positions 122.

The pipette stand positions 122 are advantageously configured to accommodate certain compatible manual pipettes as well as electronic pipettes. When manual pipettes are positioned on the pipette check station 110, the charging terminals 124 will remain disconnected. However, the non-contact status check capabilities of the pipette check station 110 will remain functional and will work with RFID-enabled manual pipettes.

As illustrated in FIG. 1, the body 112 contains the main functional components of the pipette check station 110, and in an embodiment of the invention, the body 112 may be detached from the column 114 and the base 116, and attached to a work area by clamps, magnets, or other fixation methods. Accordingly, a power connection and any wired data interfaces may be exposed on a rear surface 126 or a lower surface 128 of the body 112 of the pipette check station 110.

It should be noted that while the pipette check station 110 is illustrated in FIG. 1 and elsewhere in this description as a pipette stand, and particularly a four-channel charge stand for electronic pipettes, it may be configured in other ways as well. A stand may be configured to accommodate one or more pipettes, or only manual pipettes, or small handheld laboratory devices that are not pipettes, or it may simply take the form of a resting surface (e.g. a mat) without any specific stand or other support structure, as long as the other attributes of the invention (RFID reading capabilities and a user interface) are present in some form.

Figure 2:
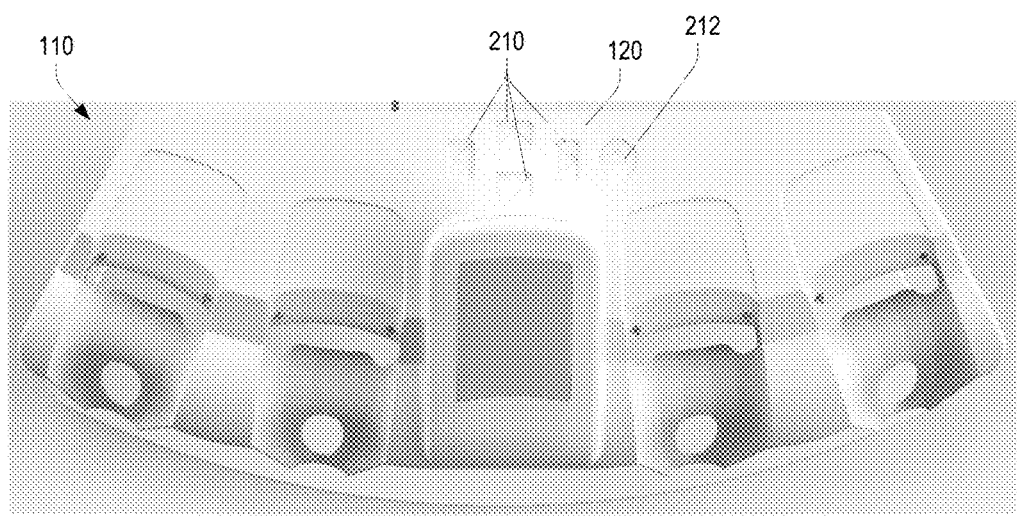
FIG. 2 is an overhead view of the pipette charge stand of FIG. 1 illustrating a centrally located display screen and a five-button user interface panel.

FIG. 2 shows a top view of the pipette check station 110 of FIG. 1. As shown, the control panel 120 includes a plurality of buttons, including a navigation pad with up, down, left, and right-pointing directional buttons 210 and a selection button 212. In a presently preferred embodiment of the invention, the control panel 120 and buttons 210, 212 are membrane-style buttons sealed against moisture intrusion, which are easy to clean and will tend to protect the electronics of the pipette check station 110 from a relatively harsh laboratory environment, while still remaining easy to actuate. As the pipette check station 110 is simple to operate without using the control panel 120 (as will be discussed in further detail below), the control panel 120 may be situated behind the raised display screen 118 with minimal impact to functionality.

Figure 3:
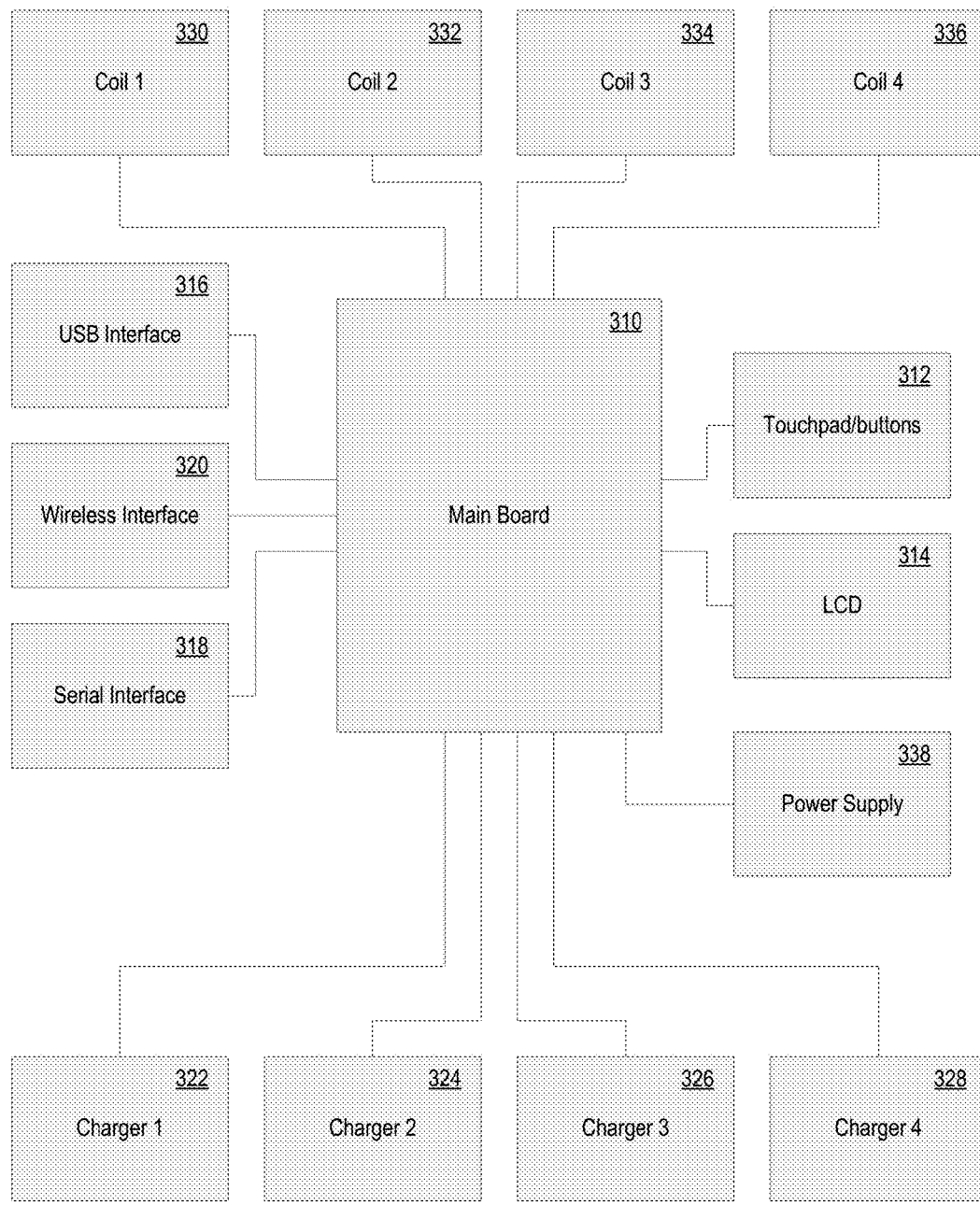
FIG. 3 is a block diagram of the electronic pipette charge stand of FIG. 1, incorporating charging circuitry and RFID reading coils for four pipettes.

FIG. 3 is a functional block diagram illustrating the high-level interaction of various subsystems in a pipette check station according to the invention.

The pipette check station 110, and in particular the main body 112 thereof, includes a main board 310 including data processing unit with a CPU, memory, some nonvolatile memory for program and configuration storage, and a real-time clock. The main board 310 also includes interfaces to a touchpad or buttons 312 (such as the control panel 120 with its directional buttons 210 and selection button 212), a liquid crystal display (LCD) 314 or other type of display screen (such as the display screen 118), a USB interface 316, a serial interface 318, and a wireless interface 320. In the disclosed embodiment of the invention, one or more of the USB, serial, or wireless interfaces 316, 318, 320 is used to connect the pipette check station 110 to a workstation (see, for example, FIG. 6 described below) for data exchange, configuration, and firmware upgrades. Accordingly, not all of these interfaces need be present, and it may be advantageous to leverage either the USB interface 316 or the serial interface 318, and especially the latter, to connect to a wireless "dongle" that may be presented as an option for the pipette check station 110 and used only when desired or necessary.

The main board 310 of the pipette check station 110 is also capable of controlling four chargers 322, 324, 326, and 328, one for each of the pipette stand positions 122 in an electronic pipette charging stand. In this configuration, concurrent or sequential charging may be managed by the CPU or other circuitry on the main board 310, but where intelligent charging capabilities are built into the compatible electronic pipettes, it may not be necessary to control the chargers 322, 324, 326, or 328. But in any case, it is considered advantageous for the pipette check station 110 to be able to query charge status from any electronic pipettes held in the four pipette stand positions (and thus, present charge status information on the display screen 118), and accordingly, the block diagram of FIG. 3 enables this functionality by ensuring the chargers 322, 324, 326, and 328 are functionally coupled to the main board 310.

The main board 310 of the pipette check station 110 is further coupled to four coils 330, 332, 334, and 336. As disclosed, the RFID transponders used in a system according to the invention are passive and must be energized by applying a signal to a coil in proximity to the RFID transponder before or while information is read from the transponder. Such RFID systems are well known in the art. In the disclosed embodiment, a pipette check station according to the invention scans for low-frequency RFID tags embedded within (or otherwise attached to) pipettes, but other types of tags and transponders, either passive or active, may be employed.

Figure 4:
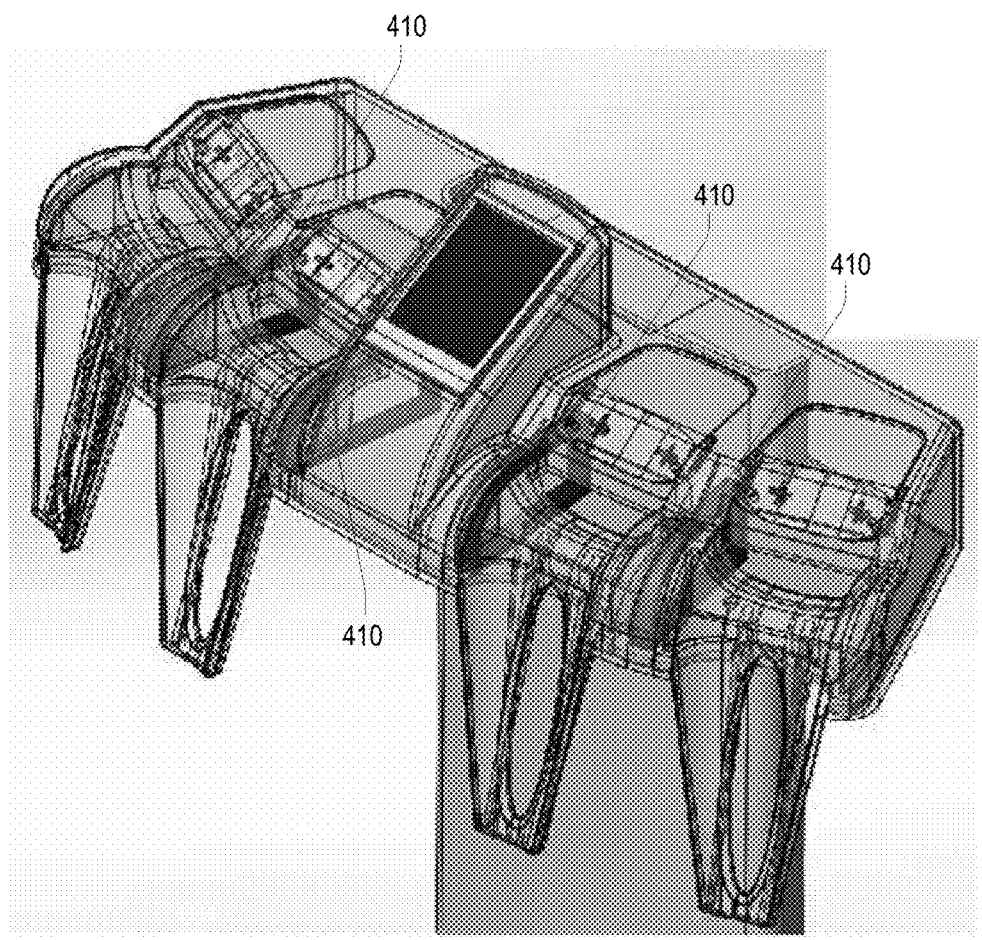
FIG. 4 is a is an internal view illustrating an exemplary arrangement of four RFID reading coils for four pipette positions in a pipette charge stand illustrated in FIG. 1.

Various coil configurations are possible for a pipette check station 110 according to the invention, and where RFID transponders are situated near a finger hook in compatible electronic and manual pipettes, it may be advantageous to position one coil under or near each finger hook as it rests in one of the pipette stand positions 122 of the pipette check station. Alternatively, as shown in FIG. 4, coils 410 may be positioned between the pipette stand positions 122, with the coils 410 energized sequentially and differential signal strength used to determine which pipette stand position 122 is being queried. If the coils 410 are energized sequentially and not simultaneously, the four coils 330, 332, 334, and 336 are preferably multiplexed and coupled to a single transmit/receive circuit on the main board 310. Other coil configurations (including various alternative positions, sizes, and shapes for the coils and number of coils needed for a multi-pipette stand) are possible and would be well understood by an engineer of ordinary skill experienced in RFID system design.

As further shown in FIG. 3, the pipette check station 110 includes a power supply 338, which would provide sufficient electrical power to supply the main board 310 and the chargers 322, 324, 326, and 328. In the disclosed embodiment, all features of the pipette check station 110 use relatively little power except for electronic pipette charging (which may itself require several amperes of power to rapidly charge four electronic pipettes simultaneously). Accordingly, the main board 310 may be energized at essentially all times, facilitating a user's review of pipette calibration and service status as contemplated by the invention at any time a pipette is placed on or removed from one of the pipette stand positions 122 of the pipette check station. In a pipette check station for manual pipettes only, battery power may be sufficient, but the power supply 338 in a four-position electronic pipette charging stand would be coupled to a suitable source, such as hardwired 110/220V power.

Figure 5:
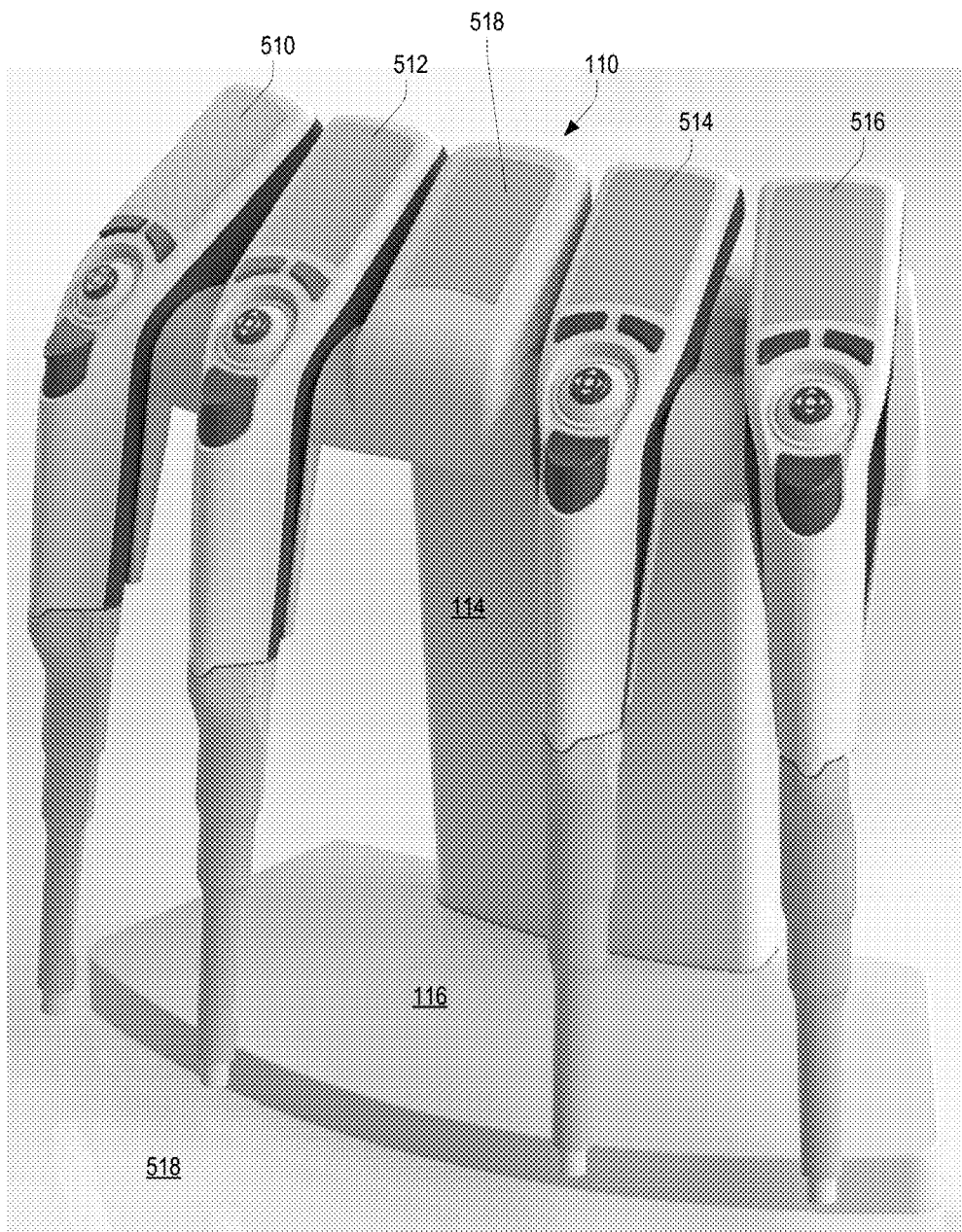
FIG. 5 shows the electronic pipette charge stand of FIG. 1 with four electronic pipettes hanging thereupon.

As shown in FIG. 5, up to four compatible electronic pipettes 510, 512, 514, and 516 may be held by a charge stand configured with a column 114 and base 116 according to the invention; the pipettes will charge either simultaneously or sequentially while so held, and the pipette check station 110 will hold the pipettes comfortably above the bench top 518 or other work surface. Information relevant to the charge status, calibration status, and service status of the pipettes will be presented on the display screen 118.

Figure 6:
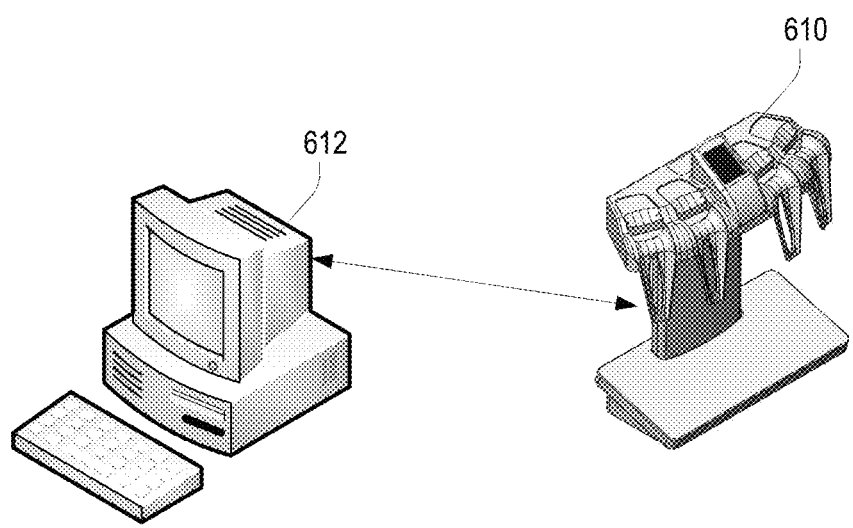
FIG. 6 is a block diagram illustrating an exemplary simple desktop configuration of a system according to the invention, with a pipette check station in communication with a computer workstation.

FIG. 6 is a block diagram of a simple system configuration for a pipette check station according to the invention, in which a single check station 610 is coupled to a single workstation 612 through the USB interface 316, serial interface 318, or wireless interface 320 of the pipette check station 610. For wireless convenience over short distances, a Bluetooth wireless connection may advantageously be used for the interface between the check station 610 and the workstation 612. However, for reliability—especially when performing firmware upgrades on the check station 610—a hardwired connection (like the USB interface 316) may be preferred.

The workstation 612 is advantageously used to configure the check station 610, and in particular may be used to set the time and date on the check station 610, to give it a memorable or otherwise useful name (especially in a laboratory setting where several check stations may be in use), and to set calibration and service date preferences and limits as described below. In a preferred embodiment of the invention laboratory equipment management software (such as LabX software from METTLER-TOLEDO) may be programmed to enable configuring the check station 610, and also to receive data from the check station 610 about the pipettes that have been scanned and their respective service and calibration statuses, which may then be stored in a database on the workstation (or elsewhere) or otherwise processed. In this way, a lab manager or other user may be empowered to track and otherwise analyze pipette usage (by observing and storing time and date for each pipette's removal from and return to the stand), and to advantageously and proactively schedule pipette calibration and service as needed.

Figure 7:
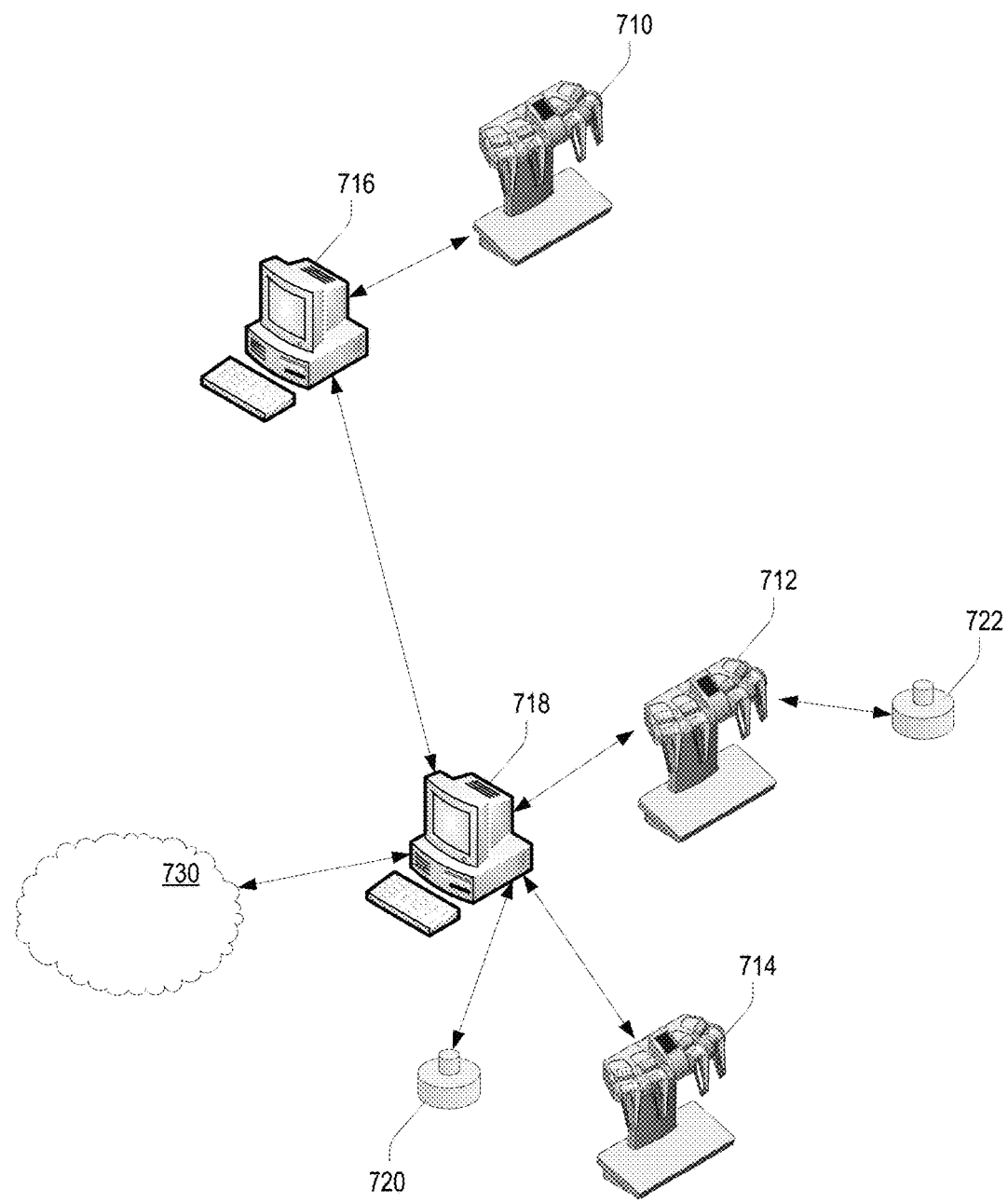
FIG. 7 is a block diagram illustrating a workgroup configuration of a system according to the invention, with multiple pipette check stations in communication with multiple computer workstations on a local-area computer network.
Figure 8:
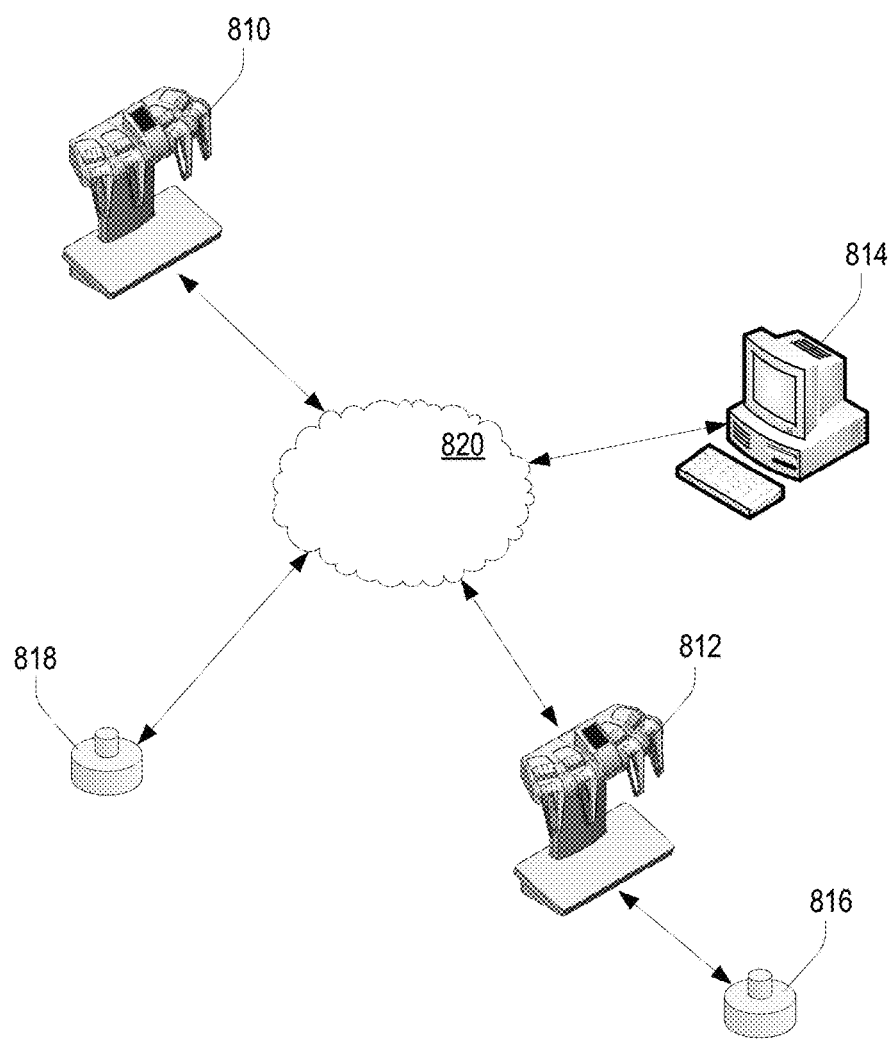
FIG. 8 is a block diagram illustrating a cloud-based configuration of a system according to the invention, with multiple pipette check stations and a workstation in communication with a cloud-based service provider.
Figure 9:
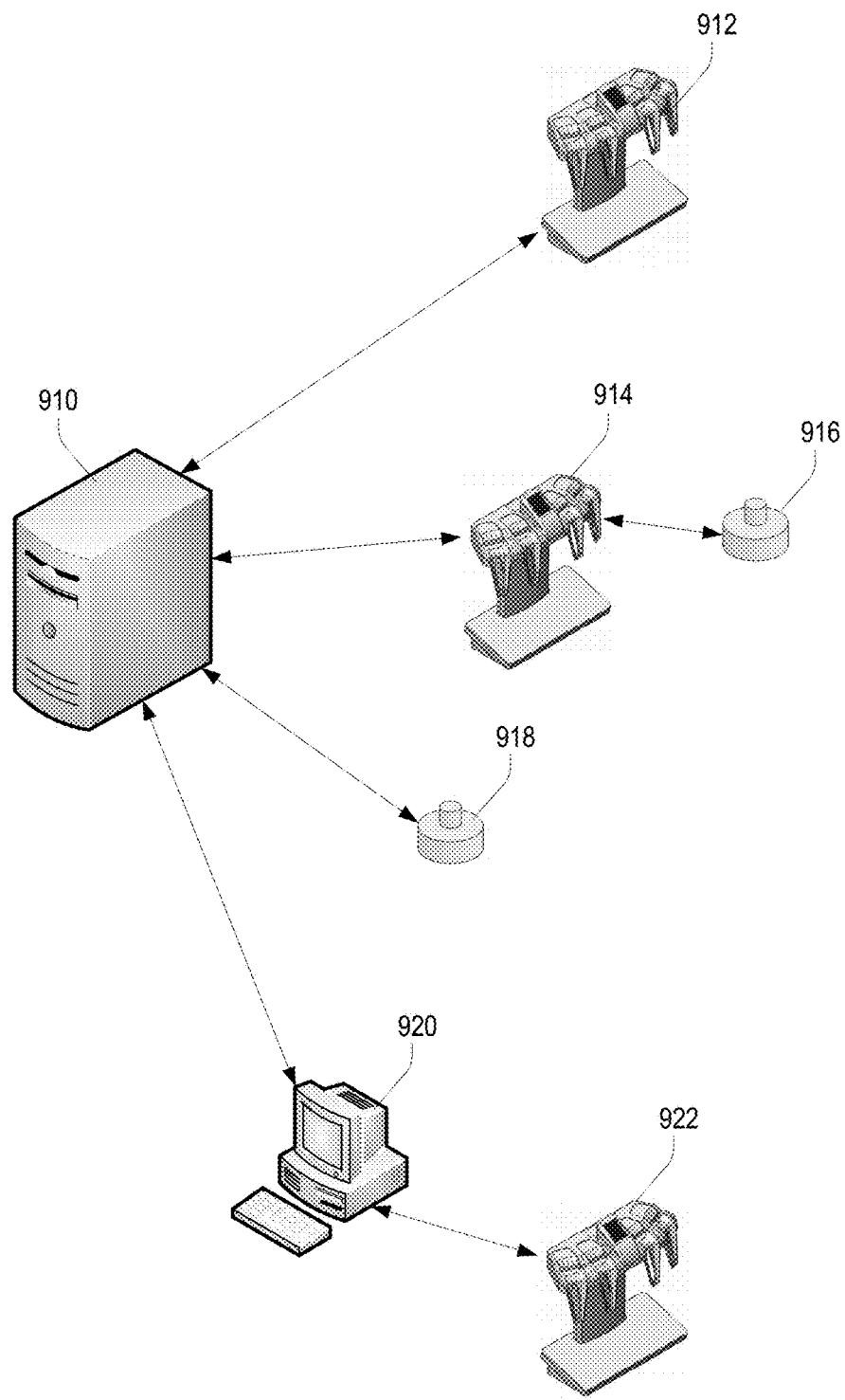
FIG. 9 is a block diagram illustrating a client-server configuration of a system according to the invention, with multiple pipette check stations and a workstation in communication with a server.

FIGS. 7, 8, and 9 illustrate alternative system configurations. FIG. 7 presents a local workgroup of devices including three pipette check stands 710, 712, and 714. A first pipette check station 710 is coupled to a first workstation 716 and is configured and operated generally as described above with reference to FIG. 6. A second pipette check station 712 and a third pipette check station 714 are connected to a second workstation 718 (which may optionally be connected to a network or the Internet 730); in this case the workstation software is programmed to be able to distinguish and operate multiple check stations. The configuration shown in FIG. 7 also includes two pipette performance check units 720 and 722; these devices include gravimetric means (e.g., a load cell or balance mechanism) or other means (such as a spectrophotometric analysis cell) to verify whether a pipette set to a certain volume is in fact accurately transferring that desired volume of liquid (within a specified tolerance), and may be configured and set up as desired through a workstation (as in the second workstation 718 coupled to a first pipette performance check unit 720) or indirectly through a pipette check station (as in the third pipette check station 714 coupled to a second pipette performance check unit 722, through a USB interface, serial interface, or wireless interface of the check station 714). Advantageously, and to the extent such pipette performance check units are connected to workstations or check stations according to the invention, the pipette performance check units need not be equipped with a user interface—all configuration and data review will be accomplished through the connected devices. In a system configuration such as that shown in FIG. 7, the laboratory equipment management software installed on the workstations 716 and 718 is preferably programmed to share and consolidate information and configuration relating to each of the check stations 710, 712, and 714 and pipette performance check units 720 and 722.

FIG. 8 shows an exemplary cloud-based configuration of a system according to the invention, including two check stations 810 and 812, a workstation 814, and two pipette performance check units 816 and 818. As illustrated, the check stations 810 and 812, the workstation 814, and one pipette performance check unit 818 are connected directly to a network or the Internet 820, and accordingly, each of these devices as illustrated will be equipped with a suitable network interface (such as Ethernet or WiFi). The network-connected devices must be configurable as to network address (or automatically configured), and the laboratory equipment management software on the workstation 814 may be programmed to do this, among other capabilities.

A server-based system configuration for check stations according to the invention is presented in FIG. 9. In this topology, a server 910 (which may be on-site with the other devices, or remotely located) is connected to a first check station 912, a second check station 914 with associated first pipette performance check unit 916, a second pipette performance check unit 918, and a workstation 920 connected to a third check station 922. As with the configuration shown in FIG. 8, the network-connected devices (including the first and second check stations 912 and 914, the second pipette performance check unit 918, and the workstation 920) should be equipped with network interfaces. Laboratory equipment management software runs on the server 910 and communicates with each of the devices illustrated in FIG. 9; the workstation may run a software client program specific to the laboratory equipment management software, or may interact with the software on the server through a web-based interface or other well-known means.

Figure 10:
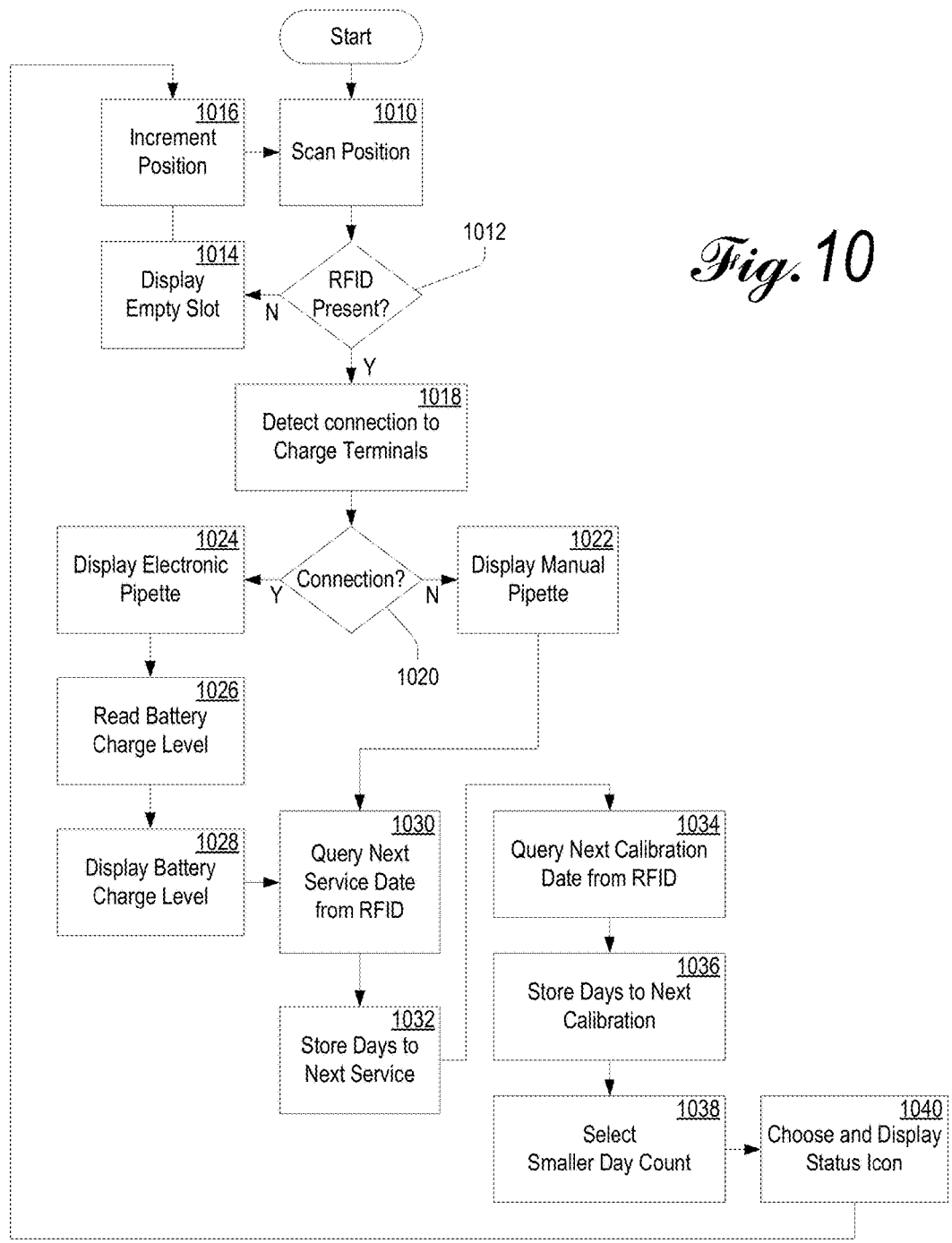
FIG. 10 is a flowchart illustrating an exemplary mode of operation for a multi-position electronic/manual pipette stand according to the invention.

FIG. 10 is a flowchart of operation for an exemplary pipette check station including four pipette stand positions 122, such as the pipette check station 110 illustrated in FIG. 1.

In the disclosed embodiment, the pipette stand positions 122 are scanned sequentially, and accordingly, the process begins by scanning a single position (step 1010). If an RFID transponder (or other compatible data storage facility) is not present (step 1012), the corresponding pipette stand position 122 is considered empty and the display screen 118 is updated to show no pipette in that position (step 1014). The position is incremented (step 1016) and the process is repeated and looped to scan each pipette stand position 122 (step 1010 and subsequent steps).

If an RFID transponder is present in any of the pipette stand positions 122 (step 1012), the pipette check station detects whether an electronic pipette is connected to the corresponding charge terminals 124 (step 1018). If a connection to the charge terminals is not detected (step 1020), a manual pipette is shown on the display screen 118 and the process continues with reading the RFID transponder (steps 1030 and subsequent steps). If a connection to the charge terminals is detected (step 1020), the battery charge level is read from the terminals 124 corresponding to the pipette stand position 122 being queried (step 1026), and the battery charge level is displayed on the display screen 118 (step 1028).

For both manual and electronic pipettes, the RFID transponder is queried to read the Next Service Date (step 1030), i.e. a date programmed into the RFID transponder when service is desired, which is generally programmed into the RFID transponder by a service provider when the pipette is serviced (or initially upon manufacture). If no Next Service Date is available from the RFID transponder, a Last Service Date may be obtained, with the Next Service Date calculated by adding a programmable service interval (e.g. one year). The Next Service Date (either obtained from the RFID transponder or calculated as set forth above) is compared to the current date stored by the check station 110, and the number of days until next service is stored in temporary data storage (step 1032).

The RFID transponder is then queried to read the Next Calibration Date (step 1034), i.e. a date programmed into the RFID transponder when calibration is desired, and generally programmed into the RFID by a calibration provider whenever calibration is performed. If no Next Calibration Date is available from the RFID transponder, a Last Calibration Date may be obtained, with the Next Calibration Date calculated by adding a programmable service interval (e.g. one year, or less in some particularly sensitive applications where calibration is critical). The Next Calibration Date (either obtained from the RFID transponder or calculated as set forth above) is compared to the current date stored by the check station 110, and the number of days until next calibration is stored in temporary data storage (step 1036).

The smaller of the two day counts (between the number of days until next service and the number of days until next calibration) is then calculated (step 1038), and an appropriate day count and visual icon are displayed on the display screen 118 (step 1040). In the disclosed embodiment, the visual icon is green if neither calibration nor service is due, yellow if either calibration or service is due, and red if either calibration or service is overdue—the icons may also be provided with graphical distinctions to aid users who are insensitive to color variations. Notwithstanding that, an embodiment of a pipette check station according to the invention can be envisioned that omits the display screen entirely, and only displays status information through a color-coded LED or other simplified visual indicator. Such a simplified pipette check station would not, of course, show battery charge level or the number of days remaining until service or calibration is required, but might represent a suitable compromise between function and expense for some categories of users.

After all required information is displayed, the process repeats by continuing to scan pipette stand locations 122 (step 1010) and to update the current date and time (and to also update the displayed pipette status information accordingly) as necessary. If no change to pipette status is observed after a programmable period of time, and no pipettes have been placed on or removed from the pipette check station, the pipette check station may power off the display unit 118 to conserve power until a pipette is placed on the check station or removed. Or if the user prefers, the display unit may remain powered on at all times so that battery, service, and calibration status can be viewed at a glance at all times.

FIGS. 11-17 show various exemplary user interface attributes of a pipette check station 110 according to the invention, and specifically a four position electronic pipette charge stand as illustrated in FIG. 1 and elsewhere.

Figure 11:
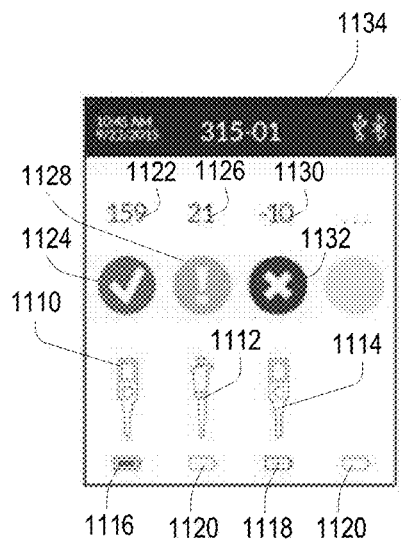
FIG. 11 is an exemplary user interface screenshot presenting status information for three pipettes on a four-position pipette stand according to the invention.

FIG. 11 shows a primary information screen on a pipette check station 110 according to the invention. This is the default screen, and it is shown whenever a pipette is added to or removed from the check station 110. As illustrated in FIG. 11, the pipette check station holds a first electronic pipette (indicated by a first representation 1110) in a first pipette stand position, a manual pipette (indicated by a second representation 1112) in a second pipette stand position, and a second electronic pipette (indicated by a third representation 1114) in a third pipette stand position. The fourth pipette stand position is vacant. The first electronic pipette is fully charged (as shown by a charged battery representation 1116) and the second electronic pipette is charging (as shown by a charging battery representation 1118). Neither the manual pipette nor the vacant pipette stand position has valid battery information, and accordingly a faded battery representation 1120 is presented.

The information screen of FIG. 11 presents various status indications in the form of colored and shaped icons. As illustrated, the first electronic pipette has 159 days until either calibration or service is needed, and accordingly the day count "159" (1122) is shown above a green check-mark icon 1124. The manual pipette has 21 days until calibration or service is required, so the day count "21" (1126) is shown above a yellow exclamation point icon 1128. The second electronic pipette is overdue for service or calibration by ten days, and accordingly the day count "−10" (1130) is shown above a red X-mark icon 1132. Therefore, the battery and service/calibration status for each of the pipettes held on the pipette check station 110 is easily viewable without operating any controls on the pipette check station 110.

The header 1134 of the display screen provides additional global information about the pipette check station, such as its programmed name, the current date and time, and interface connection status (represented by Bluetooth and USB icons).

Figure 12:
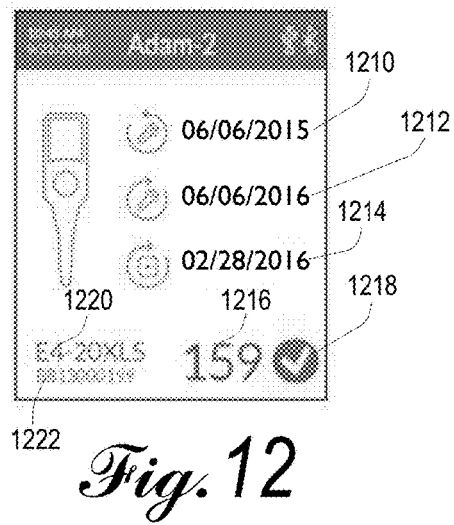
FIG. 12 is an exemplary user interface screenshot presenting detailed information for an electronic pipette captured by a check station according to the invention, in which neither service nor calibration is currently required.
Figure 13:
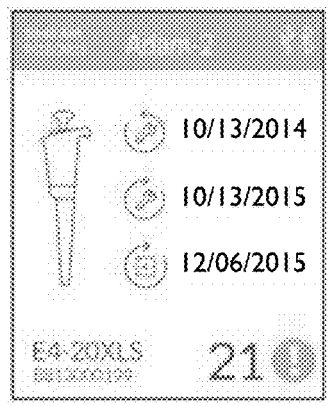
FIG. 13 is an exemplary user interface screenshot presenting detailed information for a manual pipette captured by a check station according to the invention, in which service or calibration is due to be performed.
Figure 14:
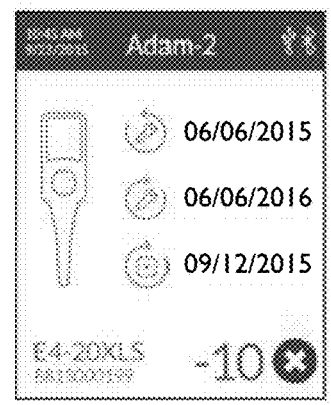
FIG. 14 is an exemplary user interface screenshot presenting detailed information for an electronic pipette captured by a check station according to the invention, in which service or calibration is overdue.

The directional buttons 210 and selection button 212 can be manipulated to select any of the pipettes for further, more detailed information. FIG. 12 shows such information relating to the first electronic pipette of FIG. 11. A first icon and date 1210 shows the last service date, a second icon and date 1212 shows the next service date, and a third icon and date 1214 shows the next calibration date. A larger day count 1216 and green check icon 1218 show the current status (as also shown in FIG. 11, calculated as shown in FIG. 10). The model number 1220 and serial number 1222 of the pipette, obtained from the RFID transponder, are also displayed. Similar information screens for the manual pipette and second electronic pipette of FIG. 11 are presented in FIGS. 13 and 14, respectively. (It should be noted that the models, serial numbers, dates, and day counts presented in FIGS. 11-14 are exemplary, used only for purposes of illustration.)

Figure 15:
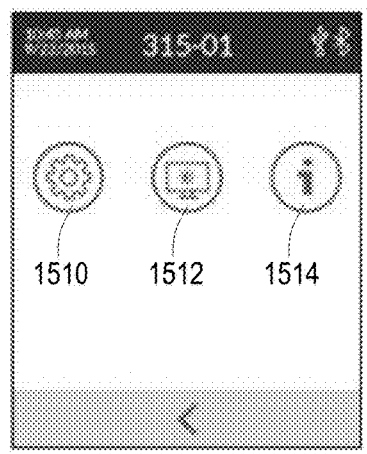
FIG. 15 is an exemplary user interface screenshot presenting a main menu for a pipette check station according to the invention.

FIG. 15 shows a main menu screen, selectable from the default information screen of FIG. 11. It presents three selectable icons: settings 1510, display brightness 1512, and information 1514. This screen of icons may be navigated by manipulating the directional buttons 210, and they will highlight on-screen as they are traversed. A desired option may be selected by depressing the selection button 212.

The display brightness icon 1512, when selected, will allow the backlight brightness for the display screen 118 to be adjusted with the directional buttons until a desired setting is obtained. The information icon 1514, when selected, will show some information about the pipette check station 110, including (for example) its serial number and firmware version number. Provisions may be provided to edit some information relating to the pipette check stand 110, but preferably, such changes will be made through laboratory equipment management software on a connected workstation or other device with a more comprehensive user interface and auditing/tracking capabilities.

Figure 16:
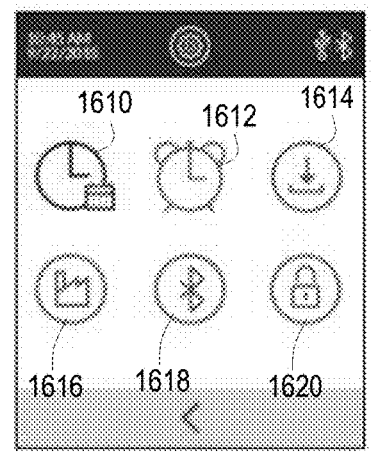
FIG. 16 is an exemplary user interface screenshot presenting a configuration menu for a pipette check station according to the invention.

The settings icon 1510, when selected, opens a configuration menu as illustrated in FIG. 16. This configuration menu contains selectable icons to set the current date and time 1610, to set service and calibration warning intervals 1612 (as described below with reference to FIG. 17), to perform a firmware upgrade 1614, to perform a factory reset 1616, to modify Bluetooth connection settings 1618 (such as to pair/unpair with other equipment, power on and off the connection, etc.), and to lock or unlock settings 1620 subject to a passcode.

Figure 17:
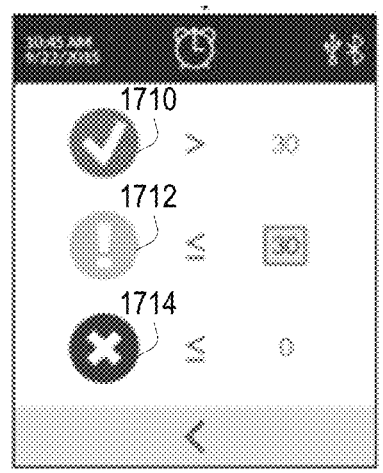
FIG. 17 is an exemplary user interface screenshot presenting a calibration or service interval setup screen for a pipette check station according to the invention.

The display screen of FIG. 17 shows user configurable service and calibration warning intervals. On the various information screens available on a pipette check station 110 according to the invention (see, e.g., FIGS. 11-14), a green check-mark icon 1710 will be shown whenever next service and calibration dates are more than thirty days in the future. This interval, when changed, also changes the interval for when the yellow exclamation point icon 1712 is shown—in this case, whenever next service or calibration date is within thirty days. A user may also select when the red X-mark icon 1714 is shown; as illustrated in FIG. 17, it will appear on or after a calibration or service due date. Any of these intervals may be adjusted as needed to facilitate the logistics necessary in taking pipettes out of service for service or calibration, or simply as desired by the user.

In an embodiment of the invention, the pipette check station 110 may be programmed with additional capabilities and user interface screens. For example, the pipette check station 110 may be programmed to recognize and configure an attached pipette performance check unit (as shown in FIGS. 7-9), for example to set one or more desired volume settings and preferred tolerances, or dates or intervals when a quick performance check (though such a unit) is required. It may also be advantageous to program a pipette check station 110 according to the invention to enable ordering service or calibration, or consumable (e.g. pipette tip) refills just by pressing a few buttons on the control panel 120— these capabilities would be able to leverage the check station's ability to recognize a pipette's model number and serial number from the RFID transponder, and would be a particular benefit when the pipette check station is located remotely from any workstation or other general purpose computer that would otherwise be usable to obtain these goods and services.

It should be observed that while the foregoing detailed description of various embodiments of the present invention is set forth in some detail, the invention is not limited to those details and a check station made, programmed, or operated according to the invention can differ from the disclosed embodiments in numerous ways. In particular, it will be appreciated that embodiments of the present invention may be employed for hand-holdable items of laboratory equipment other than pipettes, and may take forms other than pipette stands. Certain graphical elements, dates, times, and other indicia in the user interface are presented herein but may differ in practical implementation according to well understood design and engineering preferences; it should be recognized that the described and illustrated embodiment is for purposes of clarity and convenience and should not be considered limiting with respect to other embodiments or implementations of the invention. It should be noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. A pipette check station for reading service and calibration status of at least one item of hand-holdable laboratory equipment having a data storage facility, the pipette check station comprising:
   at least one antenna configured to read at least two dates representative of a next service date and a next calibration date from the data storage facility when the item is placed on the check station;
   a data processing unit programmed to calculate a first difference between the next service date and a current date and a second difference between the next calibration date and the current date; and
   a visual indicator configured to present one of a plurality of status indications based on the smaller of the first difference and the second difference;
   wherein the visual indicator presents the status indication when the item is placed on the check station.

2. The pipette check station of claim 1, wherein the item comprises a pipette.

3. The pipette check station of claim 2, wherein the wireless transponder comprises an radio frequency identification (RFID) transponder.

4. The pipette check station of claim 3, wherein the antenna comprises at least one coil capable of energizing a passive RFID transponder and reading information from the RFID transponder.

5. The pipette check station of claim 1, wherein the data storage facility comprises a wireless transponder.

6. The pipette check station of claim 1, wherein the pipette check station comprises a pipette stand.

7. The pipette check station of claim 6, wherein the pipette stand is configured as an electronic pipette charging stand capable of recharging at least one electronic pipette.

8. The pipette check station of claim 6, wherein the pipette stand is configured to hold at least one electronic pipette or at least one manual pipette.

9. The pipette check station of claim 1, further comprising a display screen, and wherein the visual indicator comprises at least one icon presented on the display screen.

10. The pipette check station of claim 1, wherein the visual indicator comprises at least one light emitting diode.

11. The pipette check station of claim 1, wherein the light emitting diode is capable of displaying a plurality of colors corresponding to the plurality of status indications.

12. The pipette check station of claim 1, wherein a first status indication is presented if the smaller of the first difference and the second difference exceeds a first interval and a second status indication is presented if the smaller of the first difference and the second difference is equal to or less than the first interval.

13. The pipette check station of claim 12, wherein a third status indication is presented if the smaller of the first difference and the second difference is less than or equal to a second interval or is negative.

14. The pipette check station of claim 13, wherein at least one of the first interval and the second interval is configurable by a user of the pipette check station.

15. The pipette check station of claim 1, further comprising a data interface.

16. The pipette check station of claim 15, wherein the data interface is configured to transmit the smaller of the first difference and the second difference to a connected device.

17. The pipette check station of claim 16, wherein the check station is programmed to track at least one removal date and time when the item is removed from the check station, and wherein the data interface is configured to transmit the removal date and time to a connected device.

18. The pipette check station of claim 16, wherein the check station is programmed to track at least one placement date and time when the item is placed on the check station, and wherein the data interface is configured to transmit the placement date and time to a connected device.

19. The pipette check station of claim 1, further comprising a network interface.

20. A method for checking service and calibration status of at least one item of hand-holdable laboratory equipment using a check station, the method comprising the steps of:
    scanning a position associated with the check station to read a data storage facility of the item of laboratory equipment;
    querying at least two dates representative of a next service date and a next calibration date from the data storage facility;
    calculating a first difference between the next service date and a current date and a second difference between the next calibration date and the current date; and
    presenting a visual service or calibration status indicator on the check station to a user, wherein the visual service or calibration status indicator is representative of the smaller of the first difference and the second difference.

21. The method of claim 20, wherein the visual service or calibration status indicator comprises an icon.

22. The method of claim 20, further comprising the steps of:
    determining whether the item of laboratory equipment is an electronic pipette;
    if the item is an electronic pipette, querying a battery level from the electronic pipette and presenting a visual battery status indicator to the user.

* * * * *